(12) United States Patent
Armstrong et al.

(10) Patent No.: US 7,418,876 B2
(45) Date of Patent: Sep. 2, 2008

(54) OSCILLATORY MOTION BASED MEASUREMENT METHOD AND SENSOR FOR MEASURING WALL SHEAR STRESS DUE TO FLUID FLOW

(76) Inventors: William D. Armstrong, 1358 Indian Hills Dr., Laramie, WY (US) 82072; Jonathan Naughton, 415 S. 25th St., Laramie, WY (US) 82070; William R. Lindberg, 619 S. Eleventh, Laramie, WY (US) 82072

( * ) Notice: Subject to any disclaimer, the term of this patent is extended or adjusted under 35 U.S.C. 154(b) by 195 days.

(21) Appl. No.: 10/557,999

(22) PCT Filed: May 20, 2004

(86) PCT No.: PCT/US2004/015904
§ 371 (c)(1),
(2), (4) Date: Nov. 18, 2005

(87) PCT Pub. No.: WO2004/106844
PCT Pub. Date: Dec. 9, 2004

(65) Prior Publication Data
US 2007/0034014 A1    Feb. 15, 2007

Related U.S. Application Data

(63) Continuation of application No. 60/472,347, filed on May 21, 2003.

(51) Int. Cl.
*G01N 3/24* (2006.01)
(52) U.S. Cl. ........................................ 73/841
(58) Field of Classification Search ............ 73/841–842
See application file for complete search history.

(56) References Cited

U.S. PATENT DOCUMENTS

| | | | |
|---|---|---|---|
| 4,464,928 A | | 8/1984 | Dealy |
| 4,475,392 A | * | 10/1984 | Ajagu et al. ............... 73/866.5 |
| 4,896,098 A | * | 1/1990 | Haritonidis et al. ......... 324/663 |
| 5,052,228 A | * | 10/1991 | Haritonidis .................. 73/705 |
| 5,177,327 A | | 1/1993 | Knowles |
| 5,199,298 A | | 4/1993 | Ng et al. |
| 5,961,080 A | | 10/1999 | Sinha |
| 5,963,310 A | * | 10/1999 | Brown et al. ............... 356/35.5 |

(Continued)

*Primary Examiner*—Max Noori
(74) *Attorney, Agent, or Firm*—Emery L. Tracy

(57) ABSTRACT

A shear stress sensor for measuring fluid wall shear stress on a test surface is provided. The wall shear stress sensor is comprised of an active sensing surface and a sensor body. An elastic mechanism mounted between the active sensing surface and the sensor body allows movement between the active sensing surface and the sensor body. A driving mechanism forces the shear stress sensor to oscillate. A measuring mechanism measures displacement of the active sensing surface relative to the sensor body. The sensor may be operated under periodic excitation where changes in the nature of the fluid properties or the fluid flow over the sensor measurably changes the amplitude or phase of the motion of the active sensing surface, or changes the force and power required from a control system in order to maintain constant motion. The device may be operated under non-periodic excitation where changes in the nature of the fluid properties or the fluid flow over the sensor change the transient motion of the active sensor surface or change the force and power required from a control system to maintain a specified transient motion of the active sensor surface.

56 Claims, 4 Drawing Sheets

Schematic of dynamic resonant shear stress sensor with the governing equation and a time history of the fluctuating shear force on the sensor (from a simulation). A cutaway view of the sensor is shown to display components below the surface.

U.S. PATENT DOCUMENTS 6,341,532 B1   1/2002   Xu et al.
6,426,796 B1 * 7/2002   Pulliam et al. .............. 356/501

2003/0106379 A1 * 6/2003 Johnson et al. ............... 73/841

* cited by examiner

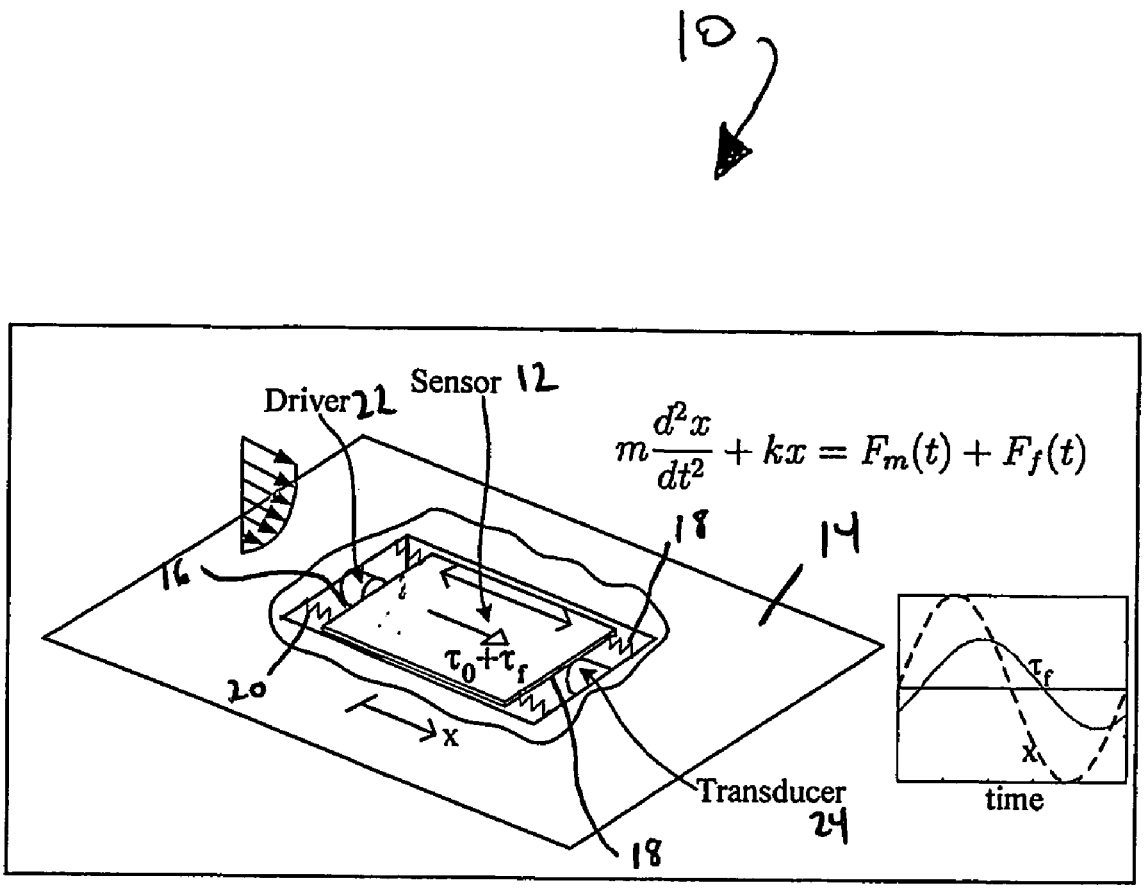
Fig. 1 - Schematic of dynamic resonant shear stress sensor with the governing equation and a time history of the fluctuating shear force on the sensor (from a simulation). A cutaway view of the sensor is shown to display components below the surface.

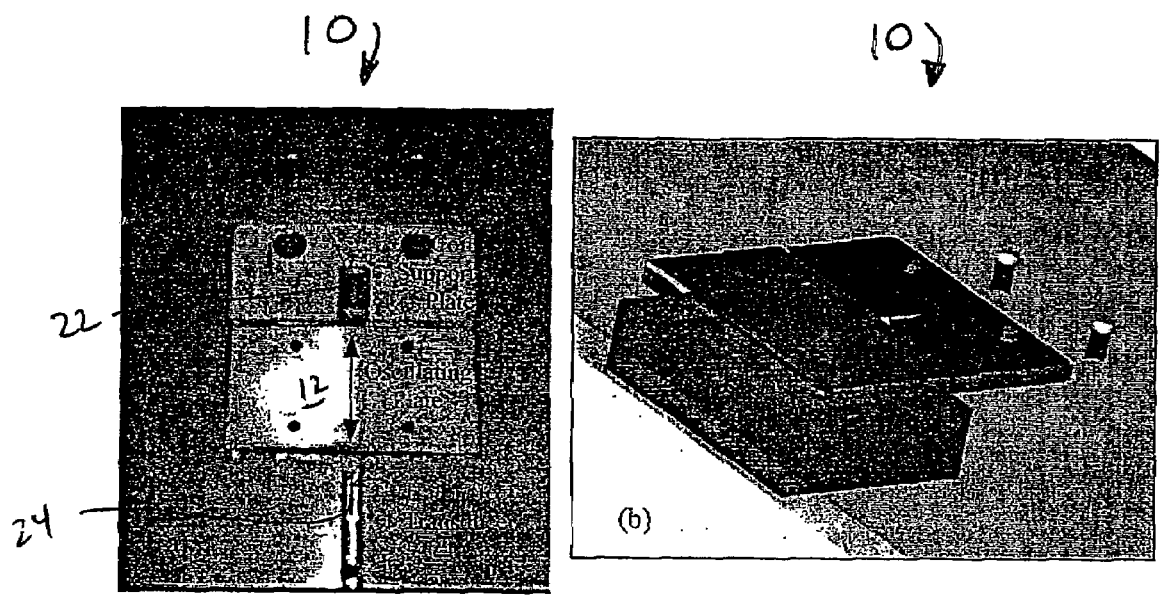
Fig. 2 - Large-scale prototype surface shear stress sensor: (a) image of the sensor, and (b) three-dimensional schematic.

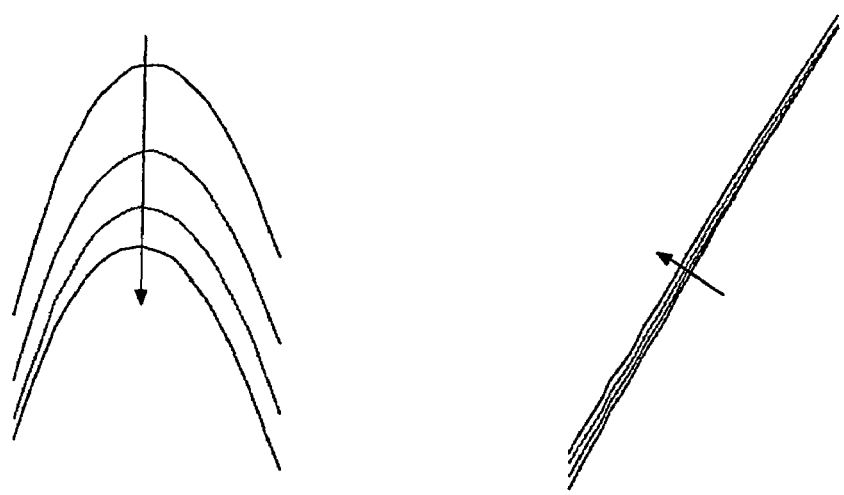
Fig. 3 - Experimental data showing the performance of an open loop, periodic, resonant wall shear stress sensor. The dependence of the sensor oscillation amplitude and phase angle on wall shear stress is shown.

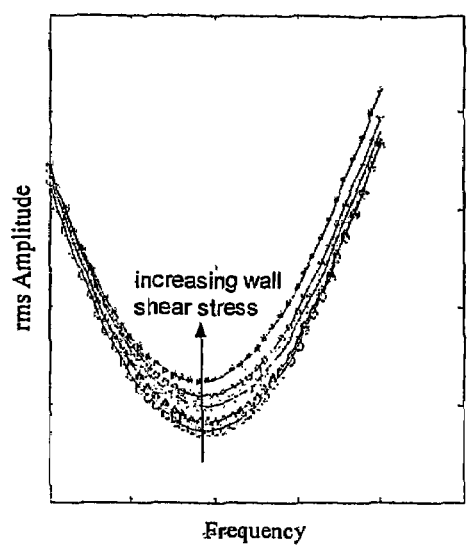
Fig. 4 - Experimental data showing the performance of an closed loop, periodic, resonant wall shear stress sensor. The dependence of the driving mechanism amplitude on frequency is shown.

OSCILLATORY MOTION BASED MEASUREMENT METHOD AND SENSOR FOR MEASURING WALL SHEAR STRESS DUE TO FLUID FLOW

The present application is a continuation of pending provisional patent application Ser. No. 60/472,347, filed on May 21, 2003, entitled "Dynamic Resonant Surface Fluidic Shear Stress Sensor".

CONTRACTUAL ORIGIN OF THE INVENTION

This invention was made with U.S. Government support under Contract No. DE-FC02-91ER75680 awarded by the U.S. Department of Energy. The U.S. Government has certain rights in this invention.

BACKGROUND OF THE INVENTION

1. Field of the Invention

This invention relates generally to a shear stress sensor and, more particularly, the invention relates to a dynamic resonant wall shear stress sensor having high bandwidth, high spatial resolution, and high sensitivity capable of fluctuating wall shear stress measurements in all kinds of fluid flows on all kinds of surfaces.

2. Description of the Prior Art

The measurement of unsteady wall shear stress (also called surface shear stress or skin friction) remains one of the great unsolved problems in experimental fluid mechanics. This is in spite of the long history of development of wall shear stress measurement techniques by some of the greatest fluid mechanics and instrumentation experts. Shear stress sensors are required for military, biomedical, and industrial applications as well as for basic understanding of wall-bounded flows. For example, it has been shown computationally that skin-friction drag can be substantially reduced using closed loop control of an actuator with feedback provided by a shear stress sensor capable of fluctuating shear stress measurements. However, no rigorously calibrated wall shear stress sensors with such capabilities exist today.

Although the measurement of wall shear stress has been studied for more than one hundred (100) years, a robust, calibrated sensor capable of measuring fluctuating shear stress is still elusive. Even with new materials and manufacturing processes that have become available over the past fifteen (15) years that enable the fabrication of miniature sensors, the expected improvements have been offset by some of the same problems larger sensors experienced as well as some new difficulties associated with the small sensors.

Table 1—Shortcomings of Some Conventional Sensors

| Direct-Force Balances | Thermal Sensors | Velocity Profile Measurement |
| --- | --- | --- |
| Small shear force | Temperature drift | Time-intensive |
| Pressure gradients | Conduction to substrate | Mean measurement only |
| Required gaps | Non-unique calibrations | Seeding sometimes required |
| Sensitivity to vibration | Reynolds analogy | Flow field access required |
| Sensitivity to | Sensitivity to | Semi-empirical |
| thermal expansion | unknown fluid composition and dust | fits susceptible to error |

Existing wall shear stress sensors can be split into two categories: conventional approaches and small-scale sensors that take advantage of the materials and manufacturing processes now available. Some sensors that have been investigated for years at large scales are being reduced in size to investigate benefits arising from scaling. Direct force balances, thermal sensors, and sensors measuring points in the velocity profile have all been investigated recently at small-scale. At the large scale, these sensors suffer from several shortcomings (see Table 1). As a result, measurement techniques such as oil-film interferometry are gaining widespread use for mean wall shear stress measurements. Due to the nature of the oil-film technique, it is likely that its use will be limited outside the laboratory environment, and it is not a candidate for fluctuating measurements.

The characteristics of an ideal wall shear stress sensor include:
High sensitivity
High Spatial Resolution
High Bandwidth
Easily Integrated
Statically and dynamically calibrated
Robust
Low power consumption
Environmentally stable Benefits of creating sensors at the small scale are possible because of the advances in microelectrical-mechanical system (MEMS) and micromachining technologies now available. The approach to date has primarily been to reduce the size of conventional sensors, and it has met with mixed success. Four approaches (velocity-based sensors, force-balance techniques, thermal, and surface acoustic wave sensors) have been attempted and are described below. For further details, consult the recent review by Naughton and Sheplak (2003).

Over the past several years, miniature velocity measurement sensors (MOEMS—Micro-Optical-Electro-Mechanical Systems) have been introduced. These sensors make streamwise velocity measurements at two or more points in the flow, and, using boundary layer similarity laws, the wall shear stress is inferred. One method uses the diverging fringe method. Measurements are made in a diverging fringe pattern created by two laser beams interfering in the near-wall region (laminar sublayer) of the boundary layer. In this region, velocity increases linearly with distance from the wall, and thus the velocity gradient is constant. Particles passing through these fringes produce a scattered light signal whose frequency is proportional to the velocity gradient. Although particles passing through the different heights have different speeds, they will produce nearly identical signals. Having obtained the velocity gradient, the wall shear stress may be easily calculated. Recent work extends this technique to higher Reynolds number by not limiting the measurement region to the laminar sublayer. Velocities are measured at two points in the boundary layer and Spalding's equation is used to fit the points and to determine the wall shear stress. For both of these methods, MOEMS enables small probe volumes and a compact sensor. The method will measure fluctuations, but the relationship of these fluctuations to variations in wall shear stress needs to be established, particularly for the two-point measurement system.

Although these methods show some promise, there are some drawbacks as well. The method requires seeding, and the need for a laser in the system limits how small the sensor can be made. These sensors will be invaluable in the laboratory for evaluating new concepts such as that suggested in the current proposal, but this sensor is unlikely to attain widespread use outside the laboratory environment.

Small-scale implementations of direct force balance methods are known. In these designs, elastic legs (tethers) support a floating element. As shear stress is applied to the sensor surface, the sensor deflects laterally. Capacitive, piezo-resistive, and optical methods have been used to determine the position of the sensor. In another method, a sensor has been developed that incorporates an electro-static comb-finger design that could be used for capacitive sensing of floating element position or could be used to actuate the sensor. A drawback of floating element designs is their limitations in dirty environments due to the necessary gaps between the floating element and the surrounding surface. Some sensors require a remote light source that makes the sensor sensitive to vibration.

In the past, small-scale silicon thermal sensors offered great promise due to their improved resistance to conduction compared to traditional, larger-scale implementations. With small-scale silicon thermal sensors, a small element is heated to a temperature above that of the flow. Changes in convective heat transfer from the sensor result in changes in the resistance of the heating element. The resistance is thus a measure of the heat transfer and is assumed to be proportional to the wall shear stress through Reynolds analogy. Only one small-scale thermal sensor has been robustly calibrated and those results were not encouraging. Thus, in order to make quantitative measurements with such sensors, a more complete understanding of coupled fluid dynamic/heat transfer processes, unsteady conduction to the substrate, temperature drift, and sensitivity to fluid transport properties is required.

The surface acoustic wave (SAW) sensor uses an oscillator that generates acoustic waves that propagate along a surface where they are sensed by an input transducer. Frequency shift in the wave is correlated to pressure and shear forces acting on the surface.

It is clear from the results to date that small-scale wall shear stress sensor development is still a work in progress. Much work has been done on these sensors, but unfortunately, few of the studies have reported rigorous characterization and calibration. Although these methods do show some promise, they are simply extensions of conventional techniques and thus inherit some of the same problems.

Accordingly, there exists a need for a dynamic resonant wall shear stress sensor capable of making measurements in fluids and having a high bandwidth. Additionally, a need exists for a dynamic resonant wall shear stress sensor having high spatial resolution. Furthermore, there exists a need for a dynamic resonant wall shear stress sensor having high sensitivity capable of fluctuating wall shear stress measurements in all kinds of flows on all kinds of surfaces.

SUMMARY

The present invention is a wall shear stress sensor for measuring the shear stress due to fluid flow over a test surface. The wall shear stress sensor is comprised of a wall shear stress sensor body and an active sensing surface. An elastic mechanism mounted between the shear stress sensor body and the active sensing surface allows movement between the shear stress body and the active sensing surface. A driving mechanism forces the active sensing surface to oscillate. A transducer measures displacement of the active sensing surface relative to the shear stress sensor body. Changes in the nature of the fluid properties or flow over the sensor measurably changes the motion of the active sensing surface, or changes the force and power required from a control system in order to maintain constant motion.

In addition, the present invention includes a sensor for measuring wall shear stress. The wall shear stress sensor comprises an oscillating plate and at least one wire attached to the sensor body that suspends the oscillating plate. A drive coil is mounted to the sensor body. A transducer is mounted to the sensor body wherein, as the plate oscillates, the transducer measures the displacement of the oscillating surface. A time varying shear force imposes drag with the magnitude of the shear drag force being different at different points within a single cycle such that the variation of shear forces within a cycle results in a dampening of the resonant forced vibration of the active sensing plate and a consequent change in oscillation amplitude and phase offset. Note: This is an actual implementation—is this important?

The present invention further includes a method for measuring wall shear stress. The method comprises providing an active sensing surface, elastically mounting the active sensing surface to the sensor body, forcing the active sensing surface to oscillate, and measuring displacement of the active sensing surface.

Furthermore, the present invention includes a method for measuring wall shear stress. The method comprising, oscillating a plate, imposing drag with time varying shear forces, dampening of resonant forced vibration of the oscillating plate with a change in oscillation magnitude and phase offset, and measuring the amplitude and/or phase offset, or measuring the change in the force and power required from a control system in order to maintain constant motion.

BRIEF DESCRIPTION OF THE DRAWINGS

FIG. 1 is a schematic view illustrating an oscillating shear stress sensor, constructed in accordance with the present invention, with a time history of the fluctuating shear force on the sensor;

FIG. 2a is a top view illustrating another embodiment of a dynamic resonant shear stress sensor, constructed in accordance with the present invention; and FIG. 2b is a side view illustrating of the shear stress sensor of FIG. 2a, constructed in accordance with the present invention;

FIG. 3 contains amplitude and phase data from an open-loop, periodic, resonant implementation of an oscillating shear stress sensor constructed in accordance with the present invention; and FIG. 4 contains amplitude data from a closed-loop, periodic, resonant implementation of an oscillating shear stress sensor constructed in accordance with the present invention.

DETAILED DESCRIPTION OF THE PREFERRED EMBODIMENTS

As illustrated in FIG. 1, the present invention is a dynamic resonant wall shear stress sensor, indicated generally at 10, for sensing changes in wall shear stress when operating near resonance.

Description of Sensor shown in FIG. 1

The wall shear stress sensor 10 of the present invention includes an active sensing surface 12 attached to the sensor body 14. Preferably, the active sensing surface 12 is connected to the sensor body 14 via elastic elements (commonly called tethers) 20 such as springs or the like mounted between the active sensing surface 12 and the sensor body 14. In the preferred embodiment, the wall shear stress sensor 10 includes four elastic legs 20 that mount the active sensing surface 12 to the sensor body 14.

In addition, the wall shear stress sensor 10 includes a driving mechanism, 22, and a transducer, 24. The driver 22 forces the active sensing surface 12 to oscillate. The transducer 24 measures the local displacement, and/or velocity, and/or acceleration of the active sensing surface 12 relative to the sensor body 14.

The fluctuating shear stress acting on the active sensing surface 12 depends on the frequency and amplitude of the shear stress sensor movement and is not in phase with the displacement or the velocity. Thus, the shear stress sensor 10 can be thought of as a weakly non-linear damped (both positive or negative) forced vibration mechanism. As a result, the active sensing surface's 12 oscillatory movement will change as the wall shear stress changes.

Capabilities of Device Described

The wall shear stress sensor 10 of the present invention is a wall shear stress sensor based on a new oscillatory motion sensing technique. Using the sensing technique, a lightweight, low-cost wall shear stress sensor 10 capable of fluctuating wall shear stress measurements has been developed. Two such wall shear stress sensors 10 mounted at and angle to each other provide shear stress magnitude and direction. Arrays of the wall shear stress sensors 10 provide spatial and temporal information about the wall shear stress field. Such wall shear stress sensors 10 are beneficial for many flow control applications. For instance, a control scheme for reducing skin-friction drag has been developed that uses wall shear stress as the sensed input to the control system. Other potential uses of the fluctuating wall shear stress sensors 10 of the present invention exist in the biomedical and industrial areas where diagnostic sensing, process and system health monitoring, and process control are important.

A number of different basic operating modes are possible with any single specific oscillating motion sensing device. Specific devices may use translation or rotary oscillatory motion or the motion that results from the distortion of the body. These include fixed input or open loop control modes, variable input or closed loop control modes, and operation under periodic or non-periodic motion. Each of these are discussed below.

Periodic Motion Operation

The wall stress sensor 10 of the present invention when operated in open-loop or closed-loop periodic modes utilizes the extremely high sensitivity of a high Q dynamic resonant-motion system to measure the wall shear stress. By definition a high Q resonant system has little damping and as a consequence high resonant vibration amplitudes occur over a narrow range of frequencies. The high Q characteristics of our device results in large amplitude periodic motion under very low periodic input forcing. The addition of small periodic force disturbances such as that due to the surface shear forces that are out of phase with that of the drive forcing strongly reduces the motion amplitude unless compensated for by a control system. Because of these active motion characteristics our design is categorically different than existing wall shear stress sensors that measure a shear stress by a time constant (static) displacement of a sensing surface. The extreme sensitivity of resonant systems to force disturbances increases the shear stress sensitivity of our sensor hundreds or even thousands of times over that of a comparable static displacement sensor.

Open-Loop, Periodic Motion Operation

Periodic motion dynamic systems operating at or near resonance are very sensitive to small changes in forces. The wall shear stress sensor 10 of the present invention is specifically designed such that wall shear stress on the surface of the active sensing surface 12 acts to damp the resonant system. By measuring changes in the resonance (amplitude and/or phase of sensor motion) due to a change in damping, the wall shear stress can be determined. Part of the benefit of the dynamic shear stress sensor 10 over static force balance sensors is that other forces (such as pressure differences across the sensor due to pressure gradients) affect the static motion but do not affect the dynamic motion and thus do not affect the sensitivity to wall shear stress. The sensor can also be driven by the driving mechanism 22 at frequencies well above or below resonance, although this would appear to be less desirable, resulting in a different response to the fluctuating shear stress on the active sensing surface 12.

Data from an implementation of an open loop, periodic, resonant sensor is shown in FIG. 3. In this experiment, the driving frequency was varied while the wall shear stress was varied. Repeating this measurement for several shear stress levels yielded the curves in FIG. 3. These data represent the first such measurements of a open-loop, periodic, resonant wall shear stress sensor and were acquired at the University of Wyoming using a prototype device. As is evident from the figure, an increase in wall shear stress tends to decrease the amplitude of the active sensing surface. There is a small phase change that is also observed, but this is somewhat exaggerated in the figure since this device has a resonance peak that spans a very small range of frequency.

Closed Loop, Periodic Motion Operation

Another mode in which the wall shear stress sensor 10 could be operated would use closed-loop feedback to control the motion of the active sensing surface 12. In this configuration, the force input from the driving mechanism 22 to the active sensing surface member 12 is controlled so as to result in approximate or exact specified periodic motion. As the wall shear stress changes, the magnitude and/or phase characteristics of the forcing will change. Therefore, any measure of the controlled time dependant or average force output from the driving mechanism 22 is a measure of the surface shear stress.

Data from an implementation of a closed-loop, periodic, resonant sensor is shown in FIG. 4. In this experiment, the driving frequency was varied while the wall shear stress was varied. Repeating this measurement for several shear stress levels yielded the curves in FIG. 4. These data represent the first such measurements of an open loop, periodic, resonant wall shear stress sensor and were acquired at the University of Wyoming using a prototype device. As is evident from the figure, an increase in wall shear stress tends to increase the voltage required from the driving mechanism 22 to drive the active sensing surface 12. The sensitivity is greatest around the minimum drive amplitude, which should correspond to the resonant frequency.

Open-Loop, Non-Periodic Oscillatory Motion Operation

In some situations, it may be preferable to use the wall shear stress sensor 10 in alternate modes. The wall shear stress sensor 10 could also be driven by the driving mechanism 22 in a non-periodic fashion (for example a pulse input) and measurable changes in the transient motion of the sensor can be used to determine the wall shear stress.

Closed Loop, Non-periodic Oscillatory Motion Operation

Another mode in which the wall shear stress sensor 10 could be operated would use closed-loop feedback to control the non-periodic motion of the active sensing surface 12. In this configuration, the force input from the driving mechanism 22 to the active sensing surface member is controlled so as to result in approximate or exact specified non-periodic motion. As the wall shear stress changes, the magnitude and/or phase characteristics of the forcing will change. Therefore, any measure of the controlled time dependant or output from the driving mechanism 22 is a measure of the surface shear Applicability to Many Flows and Calibration The wall shear stress sensor 10 of the present invention is a lightweight, inexpensive, scaleable wall shear stress sensor capable of high-bandwidth fluctuating shear stress measurements on many different surfaces in many different flows. The different types of flows include: (1) subsonic, transonic, supersonic, and hypersonic flows, (2) laminar and turbulent flows, (3) incompressible and compressible flows, and (4) linear or non-linear rheology fluids. To achieve this goal, the wall shear stress sensor 10 is calibrated both statically and dynamically by in situ dynamic calibration and/or other means.

The benefits of the wall shear stress system's 10 dynamic-resonant design are that, unlike many sensors, the wall shear stress sensor 10 is directly sensitive to wall shear stress (it is a direct sensing method) and thus can provide measurements in flows with varying temperature, varying composition, contamination, etc. It can also be used in separated flows. Thus, the wall shear stress sensor 10 can be applied in an extremely wide range of applications.

Since fluctuating wall shear stress is very sensitive to the state of the boundary layer, its measurement is key to providing the sensing necessary to control wall-bounded flows. Wall shear stress is very sensitive to, and therefore a good indicator of, the flow conditions above the surface. Therefore, miniature wall shear stress sensors 10 are effective tools useful for diagnostic purposes, flow monitoring, and flow control. The novel wall shear stress sensor 10 described in the present application is specifically designed to take advantage of the small sensor sizes possible with today's manufacturing methods.

Description of Specific Device

In an embodiment of the present invention, as illustrated in FIGS. 2a and 2b, the shear stress sensor 10 is simple and robust—it contains only four (4) major elements. The first element is a very thin, lightweight oscillating active sensing surface 12. Very fine, high tensile strength wires 20 suspend the oscillating plate 12. The longitudinal motion of the oscillating plate 12 is driven at or near the resonant frequency by a fixed frequency, electromagnetic drive coil 22. A linear Hall effect transducer 24 continuously measures the position of the device. As the surface plate 12 oscillates, time varying wall shear stress imposes a force. The magnitude of this shear force is different at different points within a single cycle. The variation of shear forces within a cycle results in a dampening of the resonant forced vibration of the oscillating plate and a consequent change in oscillation amplitude and phase offset, or result in a change in the force and power required from a control system in order to maintain constant motion. Depending on the implementation, either the change in oscillation amplitude or phase offset, or the change in required force and power is large and easily measured by standard analog or digital electronics.

Preferably, the oscillating plate 12 is located just ahead of an inset plate that contains a small solenoidal winding. During operation, the oscillating plate 12 vibrates at approximately twenty-seven (27 Hz) Hertz with longitudinal displacement amplitude of approximately three (3 mm) millimeters. In this embodiment of the present invention, the shear stress sensor 10 requires a vertical inset to accommodate a vertical elastic suspension. The wall shear stress sensor 10 is mated to the primary flow surface plate with precision, as the flow must not separate in front of the oscillating plate 12.

Scaling

An important extension of the present invention is to take advantage of scale to make the dynamic-resonant sensor effective for measuring fluctuating wall shear stress. As the size of the wall shear stress sensor 10 decreases, the frequencies at which it will resonate increase thereby increasing sensor bandwidth. Additionally, this smaller scale, higher frequency wall shear stress sensors 10 will have a reduced sensitivity to lower frequency external noise and vibration. In other cases, the scale of the flow may dictate the use of a larger size sensor. As a result, the active sensing surface 12 of the wall shear stress sensor 10 could vary in size by several (10-12) orders of magnitude depending on the application whose requirements might range from small size and high frequency response to large size and low frequency response.

Methods of Fabrication

The large range of appropriate sizes of these sensors necessitates the use of many different specific fabrication methods and materials. These may include but are not limited to, (1) mm or larger scale devices fabricated from metals, ceramics, glass, or plastics, and (2) silicon based, micron scale micro-electro-mechanical devices, and (3) nanometer scale nano-electro-mechanical devices including those that are utilize carbon or inorganic nano-wires or nano-tubes.

Methods of Forcing

The large range of appropriate sizes of these sensors necessitates the use of many different specific forcing means. These may include but are not limited to, any mechanical, electrical, magnetic or optical methods. Mechanical methods include but are not limited to forces transmitted through solid members or machine elements such as springs, or forces transmitted through fluid media such as hydraulic or acoustic forces. The forcing may result from a change in drag characteristics by changing the active sensing element's surface properties or geometry. The forcing waveform may be periodic or non-periodic, and it may be analog or digitally based including but not limited to as pulse width modulation. The forcing mechanism may be propulsion including but not limited to that from a fluid jet, or inertial forces such as from an imbalanced rotor or an oscillating mass.

Methods of Motion and Force Transduction

The large range of appropriate sizes of these sensors necessitates the use of many different specific motion transduction means. These may include but are not limited to, mechanical, electrical, magnetic, radiative, or any form of optical transduction including but not limited to those based on encoders, polarizers, moire patterns, interferometery, graded density filters, liquid crystals, apertures, reflective surfaces or imaging. The motion transduction means may be in analog, digital, continuous or discontinuous form.

Methods of Force Transduction

In a closed-loop feedback system a measure of the time-dependant forcing becomes a measure of the shear stress. Therefore some means for determining the instantaneous or average forcing is required. This may be accomplished by directly measuring the force on the active sensor surface member by a transducer including but not limited to a load cell, or by indirectly measuring the force on the active sensor surface member by measuring the input into the forcing means. This may include but is not limited to measuring the voltage or current supplied to an electro-magnetic coil.

Summary

In sum, the development of new concepts for sensing wall shear stress is long overdue. The wall shear stress sensor 10 of the present invention measures small shear forces using a driven dynamic sensor. By having the wall shear stress sensor 10 oscillate in a plane tangential to the wall shear stress, the wall shear stress sensor 10 is very sensitive to changes in wall shear stress since this additional force acts as a complex time-dependent force on the sensor. Response of the resonant system can be measured and is linked to the wall shear stress. Also, the wall shear stress sensor 10 is largely insensitive to the pressure gradient, a large source of error for some previous approaches. The wall shear stress sensor 10 of the present invention is a wall shear stress sensor with high bandwidth, high spatial resolution, and high sensitivity capable of fluctuating wall shear stress measurements in all kinds of flows on all kinds of surfaces.

Novelty of Design, Impact, Applications

The wall shear stress sensor 10 employs a novel sensing approach and is not just an incremental improvement to an existing method. The wall shear stress sensor 10 of the present invention when operated in open-loop or closed-loop periodic modes is the first sensor to utilize the extremely high sensitivity of a high Q dynamic resonant-motion system to measure wall shear stress.

The wall shear stress sensor 10 has several desired characteristics: (1) small size, (2) enhanced sensitivity, (3) good temporal resolution, (4) insensitivity to pressure gradient, (5) may be assembled into compact, multi-directional arrays, and (6) may be combined with actuators in a closed-loop control system.

As a result of the wall shear stress sensor's 10 characteristics, its impact is potentially large with application to basic research as well as in the aerospace, hydrodynamic, biomedical, and industrial fields. For example, as discussed above, the medical field has interest in wall shear stress measurements in arteries where low mean levels of and/or high fluctuations of wall shear stress are associated with plaques that form as part of arteriosclerosis. The aerospace industry is also interested in such wall shear stress sensors 10 for vehicle health monitoring (sensing problems before they occur) and flow-control applications. Other applications for these sensors include skin friction drag reduction and high sensitivity stall detection. This latter application would be particularly important for high-altitude subsonic aircraft that operate near stall.

The wall shear stress sensor 10 of the present invention has many advantages. Any process where pressure and mass flow are measured would be a candidate for a wall shear stress sensor 10. This represents an enormous number of applications. Since it is possible to manufacture the wall shear stress sensors 10 as single sensors, in large arrays, and in sensor/actuator systems, the wall shear stress sensors 10 can be applied to new areas where no equivalent technology exists today. One application for small-scale wall shear stress sensors 10 is the aerospace industry where vehicle health monitoring and flow-control applications could benefit from this sensor. A specific application would be a sensing system for stall that would be much more sensitive that today's methods. This would be particularly important for high-altitude subsonic aircraft that operate near stall. The medical field also has interest in wall shear stress measurements in arteries where low mean levels of and/or high fluctuations of wall shear stress are associated with plaques that form as part of arteriosclerosis. The industrial field could benefit from such a sensor in process monitoring and control applications. Another application would be sensing wall shear stress in coordination with sensors for detecting chemical and biological agents. The shear stress sensors 10 would monitor and/or control the air passing by the biological/chemical sensor by sensing the state of the flow.

An example where wall shear stress has been applied in an industrial process for monitoring and process control is polymer extrusion. An application with significant potential that could benefit from accurate fluctuating wall shear stress sensing would be catalyst beds. In this application, wall shear stress sensors 10 would monitor the wall shear flow just ahead of or just exiting a flow-through catalyst bed. This will allow for the continuous optimization of the target chemical process in situations where the flow properties are changing due to the degradation of the catalyst media. The wall shear stress sensors 10 may be arranged on the walls or on baffles so that a large matrix of local flow conditions may be continuously measured, which allows for the identification of local flow blockage. The present industrial method of using turbine flow meters or orifice pressure sensors is insensitive to local flow variations, exacts pressure losses, and is prone to breakdown from mechanical failure or chemical attack.

Potentially the largest beneficiary of the wall shear stress sensor 10 is industry. Since the wall shear stress sensor 10 directly measures shear stress, it can be adapted to work in challenging environments such as dusty flows and flows with mixed composition. The wall shear stress sensor 10 can be used for process control in polymer extrusion. In industrial flows, there is also a need to characterize and monitor flows, such as concentrated suspensions, in manufacturing processes. In one study, the Theological characteristics of the chocolate that are needed to produce a good product were considered. An example of how the wall shear stress sensor 10 might be used in this type of application is to monitor a flow's viscosity if the velocity profile is known (i.e. laminar pipe flow and the mass flow is known).

Summary

The foregoing exemplary descriptions and the illustrative preferred embodiments of the present invention have been explained in the drawings and described in detail, with varying modifications and alternative embodiments being taught. While the invention has been so shown, described and illustrated, it should be understood by those skilled in the art that equivalent changes in form and detail may be made therein without departing from the true spirit and scope of the invention, and that the scope of the present invention is to be limited only to the claims except as precluded by the prior art. Moreover, the invention as disclosed herein, may be suitably practiced in the absence of the specific elements that are disclosed herein.

What is claimed is:

1. A wall shear stress sensor for measuring wall shear stress, the wall shear stress sensor comprising:
    a sensor body;
    an active sensing surface on the sensor body;
    elastic means mounted between the active sensing surface member and the sensor body for allowing movement between the active sensing surface and the sensor body;
    a driving means for forcing the active sensing surface to periodically oscillate or to perform non-periodic transient motion; and
    a measuring means for measuring the position, and/or velocity, and/or acceleration of the active sensing surface relative to the sensor body, or to measure the time dependant force (or forces) between the oscillating active sensing surface member and the sensor body.

2. The wall shear stress sensor of claim 1 wherein the methodology of the active sensing device is applicable to active surfaces from sub-nanometer or single atom to tens of meters in size.

3. The wall shear stress sensor of claim 1 wherein the active sensing surface performs in a range of flows: (1) laminar and turbulent flows; (2) subsonic, transonic, supersonic and hypersonic flows; (3) incompressible and compressible flows; and (4) linear or non-linear rheology fluids.

4. The wall shear stress sensor of claim 1 wherein the motion of the sensing surface is selected from the group consisting of periodic, non-periodic, transient, translational and rotational, and result from the distortion of the body.

5. The wall shear stress sensor of claim 1 wherein the measuring means is selected from the group consisting of mechanical, electrical, magnetic, and radiative.

6. The wall shear stress sensor of claim 5 wherein the measuring means is optical transduction.

7. The wall shear stress sensor of claim 6 wherein the optical transduction is selected from the group consisting of encoders, polarizers, moire patterns, interferometery, graded density filters, liquid crystals, apertures, reflective surfaces, and imaging.

8. The wall shear stress sensor of claim 1 wherein the measuring means is selected from the group consisting of analog, digital, continuous form, and discontinuous form.

9. The wall shear stress sensor of claim 1 wherein the driving means is selected from the group consisting of mechanical, electrical, magnetic, and optical.

10. The wall shear stress sensor of claim 9 wherein the mechanical driving means is selected from the group consisting of forces transmitted through solid members and machine elements selected from the group consisting of springs and forces transmitted through fluid media selected from the group consisting of hydraulic and acoustic forces.

11. The wall shear stress sensor of claim 10 wherein the forces result from a change in drag characteristics.

12. The wall shear stress sensor of claim 11 wherein the forcing waveform is selected from the group consisting of periodic and non-periodic.

13. The wall shear stress sensor of claim 11 wherein the forcing waveform is selected from the group consisting of analog and digital.

14. The wall shear stress sensor of claim 11 wherein the forcing waveform is pulse width modulation.

15. The wall shear stress sensor of claim 1 and further comprising:
    a forcing mechanism.

16. The wall shear stress sensor of claim 15 wherein the forcing mechanism is selected from the group consisting of fluid jet and inertial forces selected from the group consisting of an imbalanced rotor and an oscillating mass.

17. The wall shear stress sensor of claim 1 wherein the force given to the active sensor surface member is measured by directly measuring the force on the active sensor surface member by a transducer.

18. The wall shear stress sensor of claim 17 wherein the measuring of the force is selected from the group consisting of a load cell and by indirectly measuring the force on the active sensor surface member by measuring the input into the forcing means.

19. The wall shear stress sensor of claim 18 wherein the indirect measurement of the force is selected from the group consisting of voltage and current supplied to an electro-magnetic coil.

20. The wall shear stress sensor of claim 1 wherein the sensor is a mm scale devices fabricated from a material selected from the group consisting of metals, ceramic, glass, and or plastic.

21. The wall shear stress sensor of claim 1 wherein the sensor is a silicon based, micron scale micro-electro-mechanical device.

22. The wall shear stress sensor of claim 1 wherein the sensor is a nanometer scale nano-electro-mechanical device selected from the group consisting of carbon and inorganic nano-wire or nano-tube based.

23. The wall shear stress sensor of claim 1 wherein the driving means includes a driver mounted between the active sensing surface and the sensor body.

24. The wall shear stress sensor of claim 1 wherein the measuring means is a transducer mounted between the active sensing surface and the sensor body.

25. The wall shear stress sensor of claim 1 wherein the elastic means is selected from the group consisting of elastic and viscoelastic structural members.

26. The wall shear stress sensor of claim 1 wherein the elastic means includes suspension by a stationary or moving fluid or fluid filled chamber or chambers.

27. The wall shear stress sensor of claim 1 wherein the elastic means includes suspension selected from the group consisting of electric, magnetic, and gravitational forces.

28. The wall shear stress sensor of claim 1 wherein the elastic means comprises springs.

29. The wall shear stress sensor of claim 1 wherein the elastic means is selected from the group consisting of extensional and flexural structural elements.

30. The wall shear stress sensor of claim 28 wherein the springs are mounted between the active sensing surface member and the sensor body.

31. The wall shear stress sensor of claim 25 wherein at least one elastic leg or suspension element is mounted at any angle between the active sensing surface member and the sensor body.

32. A method for measuring wall shear stress, the method comprising:
    providing an active sensing surface;
    elastically mounting the active sensing surface member;
    forcing the active sensing surface to move;
    measuring or controlling the time-dependant position, and/or velocity and/or acceleration of the active sensing surface; and
    providing periodic oscillatory motion and a control system such that the variation of shear force within the motion results in a positive or negative dampening of the motion of the of the active sensing surface member and a consequent change in the time dependant forcing required to maintain approximate or exact specified periodic active sensing surface position, and/or velocity or and/or acceleration waveforms.

33. A wall shear stress sensor for measuring wall shear stress, the wall shear stress sensor comprising:
an active sensing surface member;
an elastic physical suspension for the active sensing surface member;
driving means for the active sensing surface member that produces periodic motion; and
measuring means for measuring the position, and/or velocity, and/or acceleration of the active sensing surface relative to the sensor body;
wherein, as the active sensing surface moves, time varying shear stress imposes a force with the magnitude of the shear force being different at different points and times within the periodic motion such that the variation of shear force within the motion results in a dampening of the motion of the active sensing surface member and a consequent change in the motion of the sensor.

34. The wall shear stress sensor in claim 33 wherein the sensor is operated such that changes in the nature of the fluid properties or the fluid flow over the sensor change the amplitude and/or phase of the periodic motion of the active sensor surface.

35. The wall shear stress sensor in claim 33 wherein the periodic motion of the active sensing surface is selected from the group consisting of resonant, off-resonant, and non-resonant.

36. The wall shear stress sensor of claim 33 wherein an effectively frictionless measuring means continuously measures the position and/or velocity and/or acceleration of the oscillating active sensing surface member.

37. A wall shear stress sensor for measuring wall shear stress, the wall shear stress sensor comprising:
an active sensing surface member;
an elastic or physical suspension for the active sensing surface member;
driving means for the active sensing surface member that produces periodic motion; and
measuring means for measuring the position, and/or velocity, and/or acceleration of the active sensing surface relative to the sensor body;
means for providing control feedback to the driving means such that it maintains a constant motion (amplitude and phase) of the active sensing surface;
means for measuring the time-dependent force or power provided by the driving means;
wherein, as the active sensing surface moves, time varying shear stress imposes a force with the magnitude of the shear force being different at different points and times within the periodic motion such that the variation of shear force within the motion results in a dampening of the motion of the active sensing surface member and the control system compensates for the presence of the additional damping by providing increased time dependant force or power or changing the phase relationship between forcing and motion so as to achieve approximate or exact specified motion.

38. The wall shear stress sensor of claim 37 wherein the sensor is operated with an analog control system such that the driving mechanism compensates for any change in time-dependant forces by changing the instantaneous force or power or changing the phase of the forcing to achieve approximate or exact specified periodic motion.

39. The wall shear stress sensor of claim 37 wherein the sensor is operated with a digital control system such that the driving mechanism compensates for any change in time-dependant forces by discontinuously changing the instantaneous force or power or changing the phase of the forcing to achieve approximate or exact specified periodic motion.

40. The wall shear stress sensor of claim 37 wherein the sensor is operated with a mixed analog-digital control system such that the driving mechanism compensates for any change in time-dependant forces by continuously or discontinuously changing the instantaneous force or power or changing the phase of the forcing to achieve approximate or exact specified periodic motion.

41. The wall shear stress sensor of claim 37 wherein an effectively frictionless measuring means continuously measures the position and/or velocity and/or acceleration of the oscillating active sensing surface member.

42. The wall shear stress sensor of claim 37 wherein a measure of the instantaneous force or power supplied by the driving means is related to the dampening.

43. The wall shear stress sensor of claim 37 wherein the forcing means is an electro-magnetic coil wherein a measure of the instantaneous voltage or current supplied to the driving means is related to the dampening.

44. The wall shear stress sensor of claim 37 wherein the force given to the active sensor surface member is measured by directly measuring the force on the active sensor surface member by a transducer including but not limited to a load cell, or by indirectly measuring the force on the active sensor surface member by measuring the input into the forcing means.

45. The wall shear stress sensor of claim 44 wherein the force is measured by a method selected from the group consisting of voltage and current supplied to an electro-magnetic coil.

46. A wall shear stress sensor for measuring wall shear stress, the wall shear stress sensor comprising:
an active sensing surface member;
an elastic or physical suspension for the active sensing surface member;
driving means for the active sensing surface member that produces non-periodic motion; and
means for measuring the position, and/or velocity and/or acceleration of the active sensing surface member;
wherein, as the active sensing surface moves, time varying shear stress imposes a force with the magnitude of the shear force being different at different points and times within the motion such that the variation of shear force within the motion results in a dampening of the motion of the active sensing surface member.

47. The wall shear stress sensor of claim 46 wherein the variation of shear force within the motion results in a change in the transient motion of the active sensing surface member.

48. The wall shear stress sensor of claim 46 wherein the variation of shear force within the motion results in a change in the time-dependant forcing required to maintain a specified transient motion.

49. A method for measuring wall shear stress, the method comprising:
providing an active sensing surface;
elastically mounting the active sensing surface member;
providing a driving mechanism;
forcing the active sensing surface to move with the driving mechanism; and
measuring or controlling the time-dependant position, and/or velocity and/or acceleration of the active sensing surface.

50. The method of claim 49 further comprising:
providing periodic oscillatory motion to the active sensing surface member, such that the variation of shear force within the motion results in a positive or negative dampening of the motion of the of the active sensing surface member and a consequent change in the amplitude or phase characteristics of the periodic position, and/or velocity or and/or acceleration of the active sensing surface.

51. The method of claim 49 and further comprising:
providing periodic oscillatory motion and a control system such that the variation of shear force within the motion results in a positive or negative dampening of the motion of the of the active sensing surface member and a consequent change in the time dependant forcing required to maintain approximate or exact specified periodic active sensing surface position, and/or velocity or and/or acceleration waveforms.

52. The method of claim 49 and further comprising:
providing non-periodic transient motion to the active sensing surface member, such that the variation of shear force within the motion results in a positive or negative dampening of the motion of the of the active sensing surface member and a consequent change in the transient motion of the active sensing surface member.

53. The method of claim 49 and further comprising:
providing non-periodic transient motion and a control system such that the variation of shear force within the motion results in a positive or negative dampening of the motion of the of the active sensing surface member and a consequent change in the time dependant forcing required to maintain approximate or exact specified transient active sensing surface member position, and/or velocity and/or acceleration profiles.

54. A method for measuring wall shear stress, the method comprising:
providing an active sensing surface that consists of a plate that oscillates parallel to the surface on which the sensor is to be installed;
elastically mounting the active sensing surface member;
forcing the active sensing surface to move periodically at or near resonance;
dampening of resonant forced vibration of the oscillating plate due to time varying shear forces resulting in changed oscillation magnitude or phase; and
measuring of the time-dependant position, and/or velocity and/or acceleration of the active sensing surface to determine the change in oscillation magnitude or phase.

55. A method for measuring wall shear stress, the method comprising:
providing an active sensing surface that consists of a plate that oscillates parallel to the surface on which the sensor is to be installed;
elastically mounting the active sensing surface member;
forcing the active sensing surface to move periodically at or near resonance;
dampening of resonant forced vibration of the oscillating plate due to time varying shear forces; and
measuring of the time-dependant or time-averaged force or power provided by the forcing means required to maintain approximate or exact specified periodic active sensing surface position, and/or velocity or and/or acceleration waveforms.

56. A method for measuring wall shear stress, the method comprising:
providing an active sensing surface;
elastically mounting the active sensing surface member;
forcing the active sensing surface to move;
measuring or controlling the time-dependant position, and/or velocity and/or acceleration of the active sensing surface; and
providing periodic oscillatory motion to the active sensing surface member, such that the variation of shear force within the motion results in a positive or negative dampening of the motion of the of the active sensing surface member and a consequent change in the amplitude or phase characteristics of the periodic position, and/or velocity or and/or acceleration of the active sensing surface.

* * * * *